(12) United States Patent
Nabel et al.

(10) Patent No.: US 6,218,372 B1
(45) Date of Patent: *Apr. 17, 2001

(54) METHODS FOR TREATING RESTENOSIS WITH P21

(75) Inventors: Gary J. Nabel; Zhi-yong Yang; Elizabeth G. Nabel, all of Ann Arbor, MI (US)

(73) Assignee: The Trustees of the University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/426,325

(22) Filed: Oct. 25, 1999

Related U.S. Application Data

(63) Continuation of application No. 09/031,572, filed on Feb. 26, 1998, now Pat. No. 6,057,300, which is a continuation of application No. 08/533,942, filed on Sep. 26, 1995, now Pat. No. 5,863,904.

(51) Int. Cl.[7] ............... A01N 43/04; A61K 31/70; C12N 15/00; C12N 15/63; C12N 15/85
(52) U.S. Cl. ............... 514/44; 514/44; 536/23.5; 435/320.1; 435/440; 435/455; 435/475; 435/476; 435/375
(58) Field of Search ............... 514/44; 435/320.1, 435/375, 440, 455, 475, 476; 536/23.5

(56) References Cited

U.S. PATENT DOCUMENTS

| | | | |
|---|---|---|---|
| 5,672,508 | 9/1997 | Gyuris et al. | 435/320.1 |
| 5,693,622 | 12/1997 | Wolff et al. | 514/44 |

FOREIGN PATENT DOCUMENTS

| | | |
|---|---|---|
| WO 94/09135 | 4/1994 | (WO) . |
| WO 95/18824 | 7/1995 | (WO) . |
| WO 96/25507 | 8/1996 | (WO) . |

OTHER PUBLICATIONS

Leslie A. Leinwand et al., *Trends Cardiovase. Med.*, vol. 1, No. 7, pp. 271–275 (1991).
George Palade, *Science*, vol. 189, pp. 347–357 (Aug. 1975).
Bloom et al., *A Textbook of Histology*, Eleventh Edition, p. 83, p. 279 and p. 51 (1986).
Richard N. Kitsis et al., *Proc. Natl. Acad. Sci. USA*, vol. 88, pp. 4138–4142 (May 1991).
Eliav Barr et al., *Science*, vol. 254, pp. 1507–1509 (Dec. 1991).
Hua Lin et al., *Circulation*, vol. 82, pp. 2217–2221 (Dec. 1990).
Jyotsna Dhawan et al., *Science*, vol. 254, pp. 1509–1512 (Dec. 1991).
Gyula Acsadi et al., *The New Biologists*, vol. 3, No. 1, pp. 71–81 (Jan. 1991).
Peter M. Buttrick et al., *Circulation Research*, vol. 70, No. 1, pp. 193–198 (Jan. 1992).
Gorman et al., *Science*, vol. 221, pp. 551–553 (1983).
Michael S. Parmacek et al., *The Journal of Biological Chemistry*, vol. 265, No. 26, pp. 15970–15976 (1990).
Peter G. Anderson et al., *J. Cell Biochem*, (Suppl.), vol. 13, Part E, p. 176 (1989).
T.A. Partridge et al., *Nature*, vol. 337, pp. 176–179 (Jan. 1989).
Jon A. Wolff et al., *Science*, vol. 247, pp. 1465–1468 (Mar. 1990).
Leiden et al., *Circulation*, vol. 82, p. 82 (1990) Abstract 0423.
Buttrick et al., *Circulation*, vol. 82, p. 82 (1990) Abstract 0424.
Marshal, *Science*, 269: 1050–1055, 1995.
Miller et al.,*FASEB J.*, 9: 190–199, 1995.
Culver et al., *TIG*, 10(5), 174–178, 1994.
Hodgson, *Exp. Opin. Ther. Pat.*, 5(5): 459–468, 1995.
Lafont et al., *Lancet*, 346: 1442–1443, 1995.
Etienne–Julan et al, The efficiency of cell targeting by recombinant retroviruses depends on the nature of the receptor and the composition of the artificial cell–virus linker, *Journal of General Virology* 73: 3251–3255, 1992.
Jolly, Viral vector systems for gene therapy, Cancer Gene therapy, 1:1,51–64, 1994.
Zakut et al, The tumor suppression function of p21 Waf is contained in its N–terminal half, *Oncogene*, 11:393–395, Jul. 1995.
Indolfi et al, Inhibition of cellular ras prevents smooth muscle cell proliferation after vascular injury in vivo, *Nature Medicine*, 1:(6) 541–5, Jun. 1995.
Junjie Chen, et al., "Separate Domains of p21 Involved in the Inhibition of CDK Kinase and PCNA", *Nature*, vol. 374, pp. 386–388, Mar. 23, 1995.
Aldo Di Leonardo, et al., "DNA Damage Triggers a Prolonged P53–Dependent G1 Arrest and Long–Term Induction of CIP1 in Normal Human Fibroblasts", *Genes & Development*, vol. 8, pp. 2540–2551, 1994.
Wafik S. El–Deiry, et al., "WAF1/CIP1 is Induced in P53–Mediated G1 Arrest and Apoptosis", *Cancer Research*, vol. 54, pp. 1169–1174, Mar. 1, 1994.
Wafik S. El–Deiry, et al., "WAF1, A Potential Mediator of P53 Tumor Suppression", *Cell*, vol. 75, pp. 817–825, Nov. 19, 1993.

(List continued on next page.)

*Primary Examiner*—Scott D. Priebe
*Assistant Examiner*—Peter Paras, Jr.
(74) *Attorney, Agent, or Firm*—Brinks Hofer Gilson & Lione

(57) ABSTRACT

The p21 gene encodes a cyclin dependent kinase inhibitor which affects cell cycle progression, but the role of this gene product in altering tumor growth has not been established. The present inventors have now discovered that the growth of malignant cells in vivo is inhibited by expression of p21. Expression of p21 resulted in an accumulation of cells in $G_0/G_1$, alteration in morphology, and cell differentiation.

15 Claims, 6 Drawing Sheets

OTHER PUBLICATIONS

Yong Gu, et al., "Inhibition of CDK2 Activity In Vivo by an Associated 20K Regulatory Subunit", *Nature*, vol. 366, pp. 707–710, Dec. 16, 1993.

J. Wade Harper, et al., "The P21 CDK–Interacting Protein CIP1 is a Potent Inhibitor of G1 Cyclin–Dependent Kinases", *Cell*, vol. 75, pp. 805–816, Nov. 19, 1993.

Rong Li, et al., "Differential Effects by the P21 CDK Inhibitor on PCNA–Dependent DNA Replication and Repair", *Nature*, vol. 371, pp. 534–537, Oct. 6, 1994.

Yan Li, et al., "Cell Cycle Expression and P53 Regulation of the Cyclin–Dependent Kinase Inhibitor P21", *Oncogene*, vol. 9, pp. 2261–2268, 1994.

Shou Waga, et al., "The P21 Inhibitor of Cyclin–Dependent Kinases Controls DNA Replication by Interaction with PCNA", *Nature*, vol. 369, pp. 574–578, Jun. 16, 1994.

Yue Xiong, et al., "P21 is a Universal Inhibitor of Cyclin Kinases", *Nature*, vol. 366, pp. 701–704, Dec. 16, 1993.

Hui Zhang, et al., "P21–containing Cyclin Kinases Exist in Both Active and Inactive States", *Genes & Development*, vol. 8, pp. 1750–1758, 1994.

Kornelia Polyak et al., "Cloning of $p27^{Kip1}$, a Cyclin–Dependent Kinase Inhibitor and a Potential Mediator of Extracellular Antimitogenic Signals", *Cell*, vol. 78, pp. 59–66, Jul. 15, 1994.

Hideo Toyoshima et al., "p27, a Novel Inhibitor of G1 Cyclin–Cdk Protein Kinase Activity, Is Related to p21", *Cell*, vol. 78, pp. 67–74, Jul. 15, 1994.

METHODS FOR TREATING RESTENOSIS WITH P21

BACKGROUND OF THE INVENTION

This application is a continuation of application Ser. No. 09/031,572, filed Feb. 26, 1998 now U.S. Pat. No. 6,057,300 which is a continuation of application Ser. No. 08/533,942, filed Sep. 26, 1995, now U.S. Pat. No. 5,863,904.

This invention was made in part with government support under Grant Numbers CA59327, HL43757 and DK42760, awarded from the National Institute of Health. The U.S. Government has certain rights in this invention.

FIELD OF THE INVENTION

The present invention provides methods for treating or preventing restenosis and cancer in vivo by administration of a composition comprising an expression vector containing a gene encoding p21and a pharmaceutical carrier.

DISCUSSION OF THE BACKGROUND

The identification of cell cycle regulatory proteins has been greatly facilitated by studies of mutant yeast strains with abnormalities related to cell proliferation. Among the gene products defined in yeast is Far 1 (1), whose mammalian homologue, p21, alters the activity of cyclin-dependent kinases and is implicated in cell cycle progression and senescence (2–13). p21, also known as WAF1, CIP1 or SDI1 (11,12,14,15), is a downstream target of the p53 tumor suppressor gene and has thus been implicated indirectly in malignant transformation (15–18). Induction of p53 in response to DNA damage results in G1 checkpoint arrest (16–19), at which point DNA repair is accomplished prior to DNA replication in S phase. Consistent with its presumed role as a downstream effector for p53 , p21 has been shown to inhibit proliferating cell nuclear antigen (PCNA) dependent DNA replication but not DNA repair in vitro (20).

Zhang et al, Genes & Development (1994) 8:1750) studied p21 in vitro. As p21 functions as a kinase inhibitor, it had been predicted that normal cells should contain virtually no active cyclin kinases. By demonstrating that p21-containing cyclin kinases exist in both active and inactive states, Zhang et al rationalized that p21 was involved in controlling cell cycle progression in normal cells. Zhang et al found that in fibroblasts transformed with a variety of tumor viral oncoproteins, cyclin kinases exist in a binary state [cylcin/CDK]; whereas in normal fibroblasts multiple cyclin kinases exist in quaternary complexes containing p21 [cyclin/CDK/proliferating cell nuclear antigen (PCNA)/p21]. Active complexes contain a single p21 molecule. In contrast inactive complexes possess multiple p21 subunits. Although changes in p21 stoichiometry were sufficient to account for the conversion of active to inactive complexes in vitro, Zhang et al believed that "association of cyclin knases with p21 must be intertwined with other modes of regulation in vivo." Zhang et al noted that "it is not known what effect association with noninhibitory levels of p21 might have on the function of these CDK-modifying enzymes in vivo."

WO 94/09135 describes methods and diagnostic kits for diagnosing transformation of a cell, involving detection of the subunit components of cyclin complexes. In particular, the method pertains to the interaction of cyclins, PCNA, CDKs and low molecular weight polypeptides such as p21, p19 and p16.

Despite the evidence of cyclin kinase inhibitory activity in vitro, the role of p21 in tumor formation and its ability to reverse the malignant phenotype in vivo has not been defined.

SUMMARY OF THE INVENTION

Accordingly, one object of the present invention is to provide methods for treating and preventing cancer (tumor formation) in vivo.

A second object of the present invention is to provide methods for treating and preventing restenosis in vivo.

A third object of the present invention is to provide methods to induce antitumor effects in cells through induction of terminal differentiation. This method is useful for altering expression of cell surface proteins which might potentially facilitate immune recognition of tumors or causing the secretion of factors which might secondarily inhibit cell growth.

The present inventors have now determined the role of the p21 cyclin-dependent kinase inhibitor on tumor cell growth and restenosis. p21 is induced by p53 (6,7,15–18) and has thus been implicated as a downstream effector of p53 tumor suppression (23). The present inventors provide the first direct demonstration that p21 expression is sufficient to produce these tumor and restenosis suppressor effects in vivo. p21 expression was also found to facilitate transcriptional activation by NF-κB providing a mechanism whereby p21 can directly influence the expression of genes, such as adhesion molecules, associated with differentiation. The suppression of tumor growth and restenosis as well as the induction of the differentiated phenotype arises from altered patterns of gene expression, mediated in part by NF-kB, resulting from p21 induced transcriptional regulation leading to terminal differentiation and growth arrest. Previous attempts to induce antitumor effects through induction of terminal differentiation have involved the use of cytotoxic drugs or hormones (25–28) which have had variable success in achieving this effect.

DETAILED DESCRIPTION OF THE PREFERRED EMBODIMENTS

Figure 1A:
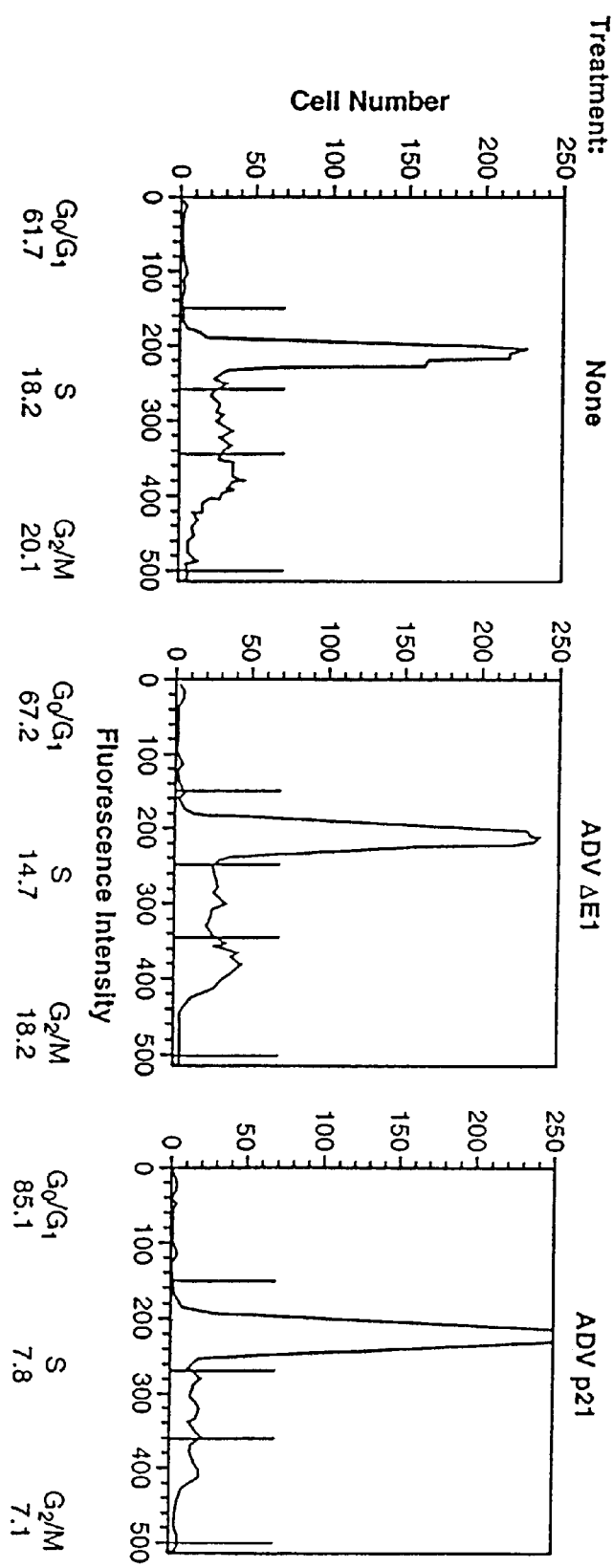
FIGS. 1A–B are graphs depicting the cell cycle analysis in malignant cell lines and expression of p21 and (B) are western blots of Renca cell lines transduced with adenoviral and eukaryotic expression vectors.

The present invention provides a method for treating cancer or restenosis comprising administering to a patient in need thereof a tumor inhibiting amount of a composition comprising:

(i) an expression vector containing the gene which encodes p21 and (ii) a pharmaceutically acceptable carrier.

The cDNA encoding p21 has been described by Xiong et al, Nature 366:701 (1993), incorporated herein by reference.

Suitable expression vectors useful in accordance with the present invention include eukaryotic and viral vectors. Useful eukaryotic vectors include pRcRSV and pRcCMV or other RSV, CMV or cellular enhancers and promoters driving expression of p21 with various polyadenylate sequences. Preferably viral vectors are used.

Viral vector systems have been indicated as highly efficient in transferring genes to mammals containing deficient genes. See, for example, Crystal Am. J. Med. 92(6A): 44S–52S (1992); Lemarchand et al., Proc. Nat'l Acad. Sci. USA 89(14):6482–6486 (1992), incorporated herein by reference. Preferably, retroviral vectors with impaired ability to replicate and transform are used. Suitable viral vectors which express p21 useful in accordance with the present invention include adenoviral vectors, Ad5–360 in combination with pAd-BglII as described by Davidson et al, Nature Gen. 3:219(1993), (incorporated herein by reference). Preferably, adenoviral vectors are used.

Preferred adenoviral vectors include: ADV described by Davidson et al, Nature Gen. 3:219(1993), (incorporated herein by reference); or other adenovirus types, including types 7001, or types 1 or 12 (as described by Ranheim et al, J. Virol. 67:2159 (1993); Green et al, Ann. Rev. Biochem. 39:701 (1970)).

The p21 can be inserted into these expression vectors and used for cell transfection using conventional recombinant techniques such as described by Sambrook, Fritsch, & Maniatis, in "Molecular Cloning, A Laboratory Manual" (2d ed): pp. E.5. (Cold Spring Harbor Press, Cold Spring Harbor, N.Y., 1989), the disclosure of which is hereby incorporated by reference. Alternatively, the expression vectors can be prepared using homologous recombination techniques as described by Davidson et al, 1993, *Nature Gen.* 3:219–223 or Lemarchand et al. Proc. Nat'l Acad. Sci. USA 89(14) :6482–6486 (1992).

The expression vectors of the present invention can additionally contain regulatory elements such as promoters and selection markers such as antibiotic resistance genes.

It is well established that viral vectors will be taken up in and integrated into cells in vivo and express the viral DNA, including inserted constructs. See, e.g., Yoshimura et al. J. Biol. Chem. 268(4):2300–2303 (1993); Crystal Am. J. Med. 92(6A):445–525 (1992); Lemarchand et al. Proc. Nat'l Acad. Sci. USA 89(14):6482–6486 (1992) the disclosures of which are hereby incorporated by reference.

In an alternate embodiment, it is also understood that other delivery systems besides expression vectors can be used to deliver p21 protein. Principally, these techniques, including the use of liposomes and DNA conjugates, are expected to provide similar delivery yields as those provided by the expression vectors discussed above. That is, rather than expressing the p21 gene via an expression vector, it is also possible to incorporate a therapeutic amount of p21 in a vehicle.

In a second alternate embodiment, p21 can be expressed as a fusion protein. In this embodiment, the gene encoding p21 is fused to a gene encoding an immunotherapeutic agent, genetic therapeutic (such as HLA-B7), protein (such as cytokines, preferably, GM-CSF, IL-2 and/or IL-12), pro-drug converting enzymes (such as thymidine kinase, cytosine deaminase and β-glucurodinase) or anticancer drug such as cis-platinum.

Fusion genes are proteins produced therefrom are described in Molecular Cloning: A Laboratory Manual, Sambrook et al, 2nd edition, Cold Spring Harbor Laboratory Press, 1989 (in particular, chapter 17) incorporated herein by reference.

Thymidine.kinase can be obtained as described in AU8776075, incorporated herein by reference. β-glucuronidase and fusion proteins thereof are described in U.S. Pat. No. 5,268,463 and U.S. Pat. No. 4,888,280, incorporated herein by reference. Cytosine deaminase and fusion proteins thereof are described in WO 9428143, incorporated herein by reference.

In addition combination therapies of viral vectors and liposomes have also shown tremendous promise and are also contemplated for use in the invention. Yoshimura et al, J. Biol. Chem., 268(4):2300–2303 (1993), incorporated herein by reference.

Liposomes are known to provide highly effective delivery of active agents to diseased tissues. For example, pharmacological or other biologically active agents have been effectively incorporated into liposomes and delivered to cells. Thus, constructs in accordance with the present invention can also be suitably formed in liposomes and delivered to selected tissues. Liposomes prepared from cationic lipids, such as those available under the trademark LIPOFECTIN (Life Technologies, Inc., Bethesda, Md.) are preferred. Particularly appealing to liposome based treatments is the fact that liposomes are relatively stable and possess relatively long lives, prior to their passage from the system or their metabolism. Moreover, liposomes do not raise major immune responses.

Thus, in one aspect of the present invention a vector containing a gene encoding p21 is incorporated into a liposome and used for the delivery of the construct to a specific tissue. The liposome will aid the construct in transfecting a cell and becoming expressed by the cell, ultimately generating p21 protein.

The composition of the present invention is a therapeutically effective amount of a vector which expresses p21 and a pharmacuetically acceptable carrier. In order to administer the viral vectors, suitable carriers, excipients, and other agents may be incorporated into the formulations to provide improved expression of p21.

A multitude of appropriate formulations can be found in the formulary known to all pharmaceutical chemists: Remington's Pharmaceutical Sciences, 15th Edition (1975), Mack Publishing Company, Easton, Pa. 18042. (Chapter 87: Blaug, Seymour). These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

Any of the foregoing formulations may be appropriate in the treatment with the viral vectors, provided that the viral particles are inactivated in the formulation and the formulation is physiologically compatible.

The amount of p21 to be administered will depend on the size of the patient and the state to which the cancer has progessed. By modifying the regulatory elements of the vector using conventional techniques or by varying the amount of viral vector titre administered, the amount of p21 expression can be adjusted to the patients needs. Typically, it is desirable to deliver approximately 50 viral vectors per cell to be treated. With the adenovirus, formulations should generally contain on the order of $10^{10}$ viral infectious units per ml. With retrovirus, slightly different titers may be applicable. See Woo et al, Enzyme 38:207–213 (1987), incorporated herein by reference. Additional assistance in determining appropriate dosage levels can be found in Kay et al, Hum. Gene Ther. 3:641–647 (1992); Liu et al, Somat. Cell Molec. Genet. 18:89–96 (1992); and Ledley et al, Hum. Gene Ther. 2:331–358 (1991), incorporated herein by reference.

Depending upon the particular formulation that is prepared for the administration of the expression vectors, administration of the compositions of the present invention can be accomplished through a variety of methods. The composition of the present invention are preferably administered by direct injection of the expression vector (or liposome containing the same) into the tumor such as described in U.S. Pat. No. 5,328,470, incorporated herein by reference.

Breast, renal, melanoma, prostate, glioblastoma, heptocarcinoma, colon and sarcoma cancer types can be treated in accordance with the present invention. Methods of diagnosis and monitoring these cancer types are well known in the art.

Arterial injury from angioplasty induces a series of proliferative, vasoactive, and inflammatory responses which can lead to restenosis. Although several factors have been defined which stimulate this process in vivo, the role of specific cellular gene products in limiting the response is not well understood. The present inventors have now found that p21 acts to limit the proliferative response to balloon catheter injury. Vascular endothelial and smooth muscle cell growth was arrested through the ability of p21 CKI to inhibit cyclin-dependent kinases and progression through the $G_1$ phase of the cell cycle. Restenosis is a clinical condition which can be diagnosised and monitored as described in Epstein et al, JACC 23(86):1278 (1994) and Landau et al, Medical Progress 330(14):981 (1994), incorporated herein by reference.

The compositions of the present invention can be used to treat all mammals, in particular humans.

The compositions of the present invention can be administered in combination with immunotherapeutic agents, genetic therapeutics (such as HLA-B7), proteins (such as cytokines, preferably, GM-CSF, IL-2 and/or IL-12), prodrug converting enzymes (such as thymidine kinase, cytosine deaminase and β-glucurodinase) and anticancer drugs such as cis-platinum. Alternatively, the compositions of the present invention can be administered in combination with expression vectors comprising genes encoding the above immunotherapeutics, genetic therapeutics, proteins, prodrug converting enzymes and anticancer drugs.

Alternatively, the compositions can be administered during adoptive cell transfer therapy.

Having generally described this invention, a further understanding can be obtained by reference to certain specific examples which are provided herein for purposes of illustration only and are not intended to be limiting unless otherwise specified.

EXAMPLES

Example 1

Use Of P21 Cycin-Dependent Kinase Inhibitor to to Treat Restenosis in Vivo

In this study, the effect of p21 expression on endothelial and smooth muscle cells in vitro and in a porcine model of arterial balloon injury in vivo was analyzed.

Cell Culture and Transfection

Primary porcine vascular endothelial and smooth muscle cells were derived from the aorta of 6-month-old domestic Yorkshire pigs and were used between the second and fifth passage. Endothelial and smooth muscle cells were grown to 70% confluence in medium 199 with 10% FBS. Cells were infected with ADV-p21 or ADV-ΔE1 (MOI 300/cell) for 1 hour in DMEM and 2% FCS, and normal media was added after 1 hour. Control cells were uninfected and carried in M199 with 10% FBS. Twenty-four hours later, the cells were split into 6 well dishes at $6 \times 10^4$ cells per well. Cells were harvested at 0, 2, 5, 7, and 10 days, and cell numbers were determined by a hemocytometer. Cell viability was assessed by trypan blue exclusion.

Cell Cycle Analysis

Cells were infected at an MOI of 300/cell with the ADV-ΔE1 or ADV-p21 vectors as described above, harvested, washed with PBS twice, and then fixed in 70% ethanol (EtOH) (King et al, Cell 79, 563–571 (1994)) for 30 minutes at 4° C. The cells were treated with 1U DNase-free RNase in 1 ml of PBS for 30 minutes at 37° C., and resuspended in 0.05 mg/ml propidium iodide (made as a 10× stock in PBS). Cells were analyzed by flow cytometry using a FACScan model (Becton Dickinson). Fluorescence measurements were accumulated to form a distribution curve of DNA content. Fluorescence events due to debris were substracted before analysis.

Adenoviral Vectors

The recombinant adenoviral vector, ADV-p21, was constructed by homologous recombination between sub360 genomic DNA, an Ad5 derivative with a deletion in the E3 region, and a p21 expression plasmid, pAd-p21. Briefly, the pAd-p21 plasmid was prepared by introducing the Hind III-XbaI fragment of a p21 expression vector utilizing the Rous sarcoma virus promoter (RSV) to regulate expression of p21 into the Bgl II site of pAd-Bgl II (Heichman & Roberts, Cell 79, 557–562 (1994)). The structure of these replication defective E1A, E1B deleted viruses was confirmed by Southern blotting. All recombinant viruses were propagated in 293 cells and purified as described (Davidson et al, 1993, Nature Gen. 3:219–223). Cesium chloride purified virus was dialysed against PBS, and diluted for storage in 13% glycerol-PBS solution to yield a final concentration of $1-3 \times 10^{12}$ viral particles/ml ($0.8-5 \times 10^{10}$ pfu/ml). All stocks were sterilized with a 0.45 μm filter and evaluated for the presence of replication competent adenovirus by infection at a MOI of 10 onto 3T3 cells. None of the stocks used in these experiments yielded replication-competent virus.

Porcine Arterial Injury

After anesthesia and intubation, domestic Yorkshire pigs (12–15 kg) underwent sterile surgical exposure of the iliofemoral arteries, and a double-balloon catheter (C.R. Bard, Inc.) was inserted into the iliofemoral artery. The proximal balloon was inflated to a pressure of 500 mmHg, measured by an on-line pressure transducer, for 5 minutes. Animals were sacrificed 1, 7, and 21 days after injury.

In Vivo Gene Transfer

Direct gene transfer was performed in the iliofemoral arteries of Yorkshire pigs using a double balloon catheter as described (Nabel et al, 1990, Science 249:1285–1288). In each animal, both iliofemoral arteries were infected with the same vector at a titer of $1 \times 10^{10}$ pfu/ml, and 0.7 ml was used in each animal (final dose of $7 \times 10^9$ pfu) (Ohno et al, 1994, Science 265:781–784; Chang et al, 1995, Science 267:518–522).

The vessel segments infected with ADV-p21 (n=28 arteries) or ADV-ΔE1 (n=28 arteries) vectors were excised 7 or 21 days later. To evaluate intimal cell proliferation, animals sacrificed at 7 days received an intravenous infusion of 5-bromo-2'-deoxycytosine (BrdC) (Sigma, St. Louis, Mo.) 25 mg/kg total dose, 1 hour prior to death. Each artery was processed in an identical manner as described (Ohno et al, 1994, Science 265:781–784). All animal experiments were performed in accordance with NIH guidelines and with approval of the University of Michigan Committee in the Use and Care of Animals.

RT-PCR Analysis

Total RNA was prepared using Trizol reagents (GIBCO/BRL) according to the manufacturer's protocol. Briefly, artery samples were homogenized in Trizol reagent. RNA was precipitated with ethanol (EtOH), washed in cold 75% EtOH three times, dried and resuspended in RNAse-free TE buffer. PCR for the p21 gene was performed (Muller et al, 1994, Circ. Res. 75:1039–1049) in the presence or absence of reverse transcriptase (RT) with the primers: 5'-GAG ACA CCA CTG GAG GGT GAC TTC G-3' (sense); and 5'-GGG CAA ACA ACA GAT GGC TGG CAA C-3'(antisense). The antisense primer was specific for recombinant p21 RNA and not endogenous porcine p21 RNA.

Measurement of Cell Proliferation and Morphometry

Measurements of cell proliferation were made 7 days after balloon injury and adenoviral infection using a monoclonal antibody to BrdC. Arterial sections were fixed, embedded, and sectioned, and immunohistochemistry using a monoclonal anti-5bromo-2'-deoxycytidine antibody was performed (Ohno et al, 1994, Science 265:781–784) to label nuclei in proliferating cells. For each artery, the number of labeled and unlabeled nuclei in the intima were quantitated using a microscope based video image analysis system (Image One Systems, Universal Imaging Corporation, Westchester, Pa.). A proliferation index was calculated as the ratio of labeled cells to total number of cells.

Intimal and medial cross sectional areas were measured in 4 sections from each artery spanning the 2 cm region of arterial injury and adenoviral infection with the image analysis system (Ohno et al, 1994, Science 265:781–784). An intima to media (I/M) area ratio for each artery was determined as the average I/M area ratio of the 4 sections.

Immunohistochemistry

Immunohistochemical studies were performed with antibodies to BrdC, smooth muscle a-actin, and p21, using methods as described (Ohno et al, 1994, Science 265:781–784; Muller et al, 1994, Circ. Res. 75:1039–1049). The following primary antibodies were used: a monoclonal mouse anti-BrdC antibody, 1:1000 dilution (Amersham Life Sciences); a monoclonal mouse anti-smooth muscle α actin antibody, 1:500 dilution (Boehringer Mannheim Biochemical); and a polyclonal mouse anti-human p21 antibody, 1:1500 dilution (Santa Cruz). Control experiments were performed using a purified mouse $IgG_{2b}$ antibody, 1:100 dilution (Promega), which did not stain the arterial specimens. Slides were developed with either a streptavidin-horseradish peroxidase complex (Vector Laboratories) or a Vectastain ABC-alkaline phosphatase reagent (Vector Laboratories), and counterstained in methyl green.

Statistical Analysis

Comparisons of intimal BrdC labeling index and I/M area ratios between ADV-p21 and ADV-AE1 arteries were made by two-tailed, unpaired t-test. Statistical significance was assumed if a null hypothesis could be rejected at the 0.05 level.

RESULTS

Expression of p21 Inhibits Vascular Cell Proliferation and Induces Cell Cycle Arrest in Vitro.

To study the effects of p21 on vascular cell growth and cell cycle distribution, quiescent porcine vascular endothelial and smooth muscle cells were infected in vitro with an adenoviral vector, ADV-p21 or a control vector containing an El deletion, ADV-ΔE1 and then stimulated to proliferate by incubation in 10% FBS. Exposure of uninfected or ADV-Δ1 infected cells to serum resulted in rapid proliferation of endothelial and smooth muscle cells. In contrast, expression of p21 in vascular endothelial and smooth muscle cells resulted in inhibition of cell proliferation by >90%; these cells were still-viable (>95%) as assessed by trypan blue exclusion. Expression of p21 in vascular endothelial and smooth muscle cells also resulted in accumulation of cells in $G_{0s}/G_1$, as assessed by propidium iodine staining. These data suggest that cells were arrested in cell cycle by p21 expression rather than p21 causing cell death.

p21 is Induced in Balloon Injured Arteries in Vivo.

To investigate the potential of p21 to regulate vascular cell growth in vivo, we first determined whether p21 expression is induced in injured arteries. Porcine iliofemoral arteries were either uninjured or injured by balloon angioplasty, and injured segments were analyzed 1, 7, and 21 days later for p21 expression, assessed by immunohistochemistry with a p21 antibody. This porcine model of arterial injury results in intimal thickening by 3 weeks (Ohno et al, 1994, Science 265:781–784). The lesion is characterized by rapid smooth muscle cell proliferation during the first 7 days after arterial injury, followed by expansion of the intima due to elaboration of extracellular matrix during the subsequent 2 weeks. Normal, uninjured porcine arteries expressed no p21. One day following arterial injury, p21 protein was not present in the intima; however, at 7 days, there was p21 protein in approximately 50% of intimal smooth muscle cells. At 21 days, p21 expression was present in lower regions of the intima, next to the internal elastic lamina, in regions where cell proliferation was not present (Ohno et al, 1994, Science 265:781–784). Indeed, p21 expression in general was inversely correlated with smooth muscle cell proliferation. These findings suggest that p21 expression is associated with arrest of vascular cell proliferation in injured arteries.

Expression of p21 In Injured Arteries Limits the Development of Intimal Hyperplasia.

To assess the direct effect of p21 on vascular cell growth in vivo, p21 vectors were introduced into porcine arteries immediately following injury. The right and left iliofemoral arteries of domestic pigs were balloon injured and infected with ADV-p21 or ADV-ΔE1 using a double-balloon catheter ($1\times10^{10}$ pfu/ml, $0.7\times10^{10}$ pfu total dose). In vivo gene transfer of ADV-p21 was demonstrated in injured porcine arteries 7 days after infection by RT-PCR analysis. p21 RNA was detected by RT PCR in infected left and right iliofemoral arteries but not in a noninfected carotid artery from the same animal or in ADV-ΔE1 noninfected and infected arteries.

The effect of p21 expression on intimal cell growth in vivo was next assessed by two methods, quantitating incorporation of BrdC into intimal cells 7 days after gene transfer and measuring I/M area ratios at 3 weeks. A 35% reduction in intimal BrdC incorporation was observed in ADV-p21 infected arteries, compared with ADv-ΔE1 arteries, 7 days after gene transfer (5.3±0.9% vs. 8.1±0.4%, p=0.035). These BrdC labeled intimal cells costained with a monoclonal antibody to smooth muscle a-actin, suggesting that inhibition of intimal smooth muscle cell proliferation was present in ADV-p21 animals. A significant reduction in I/M area ratio of 37% was observed in ADV-p21 infected arteries, compared with ADV-ΔE1 infected arteries (0.37±0.06 vs. 0.59±0.06, p=0.015). These results suggest that infection of arteries with ADV-p21 at the time of balloon injury inhibits the proliferation of intimal smooth muscle cells and significantly limits the development of a neointima.

Example 2

Use Of P21 Cycin-Dependent Kinase Inhibitor to Suppress Tumorigenicity in Vivo In this study, the effect of p21 expression on tumor growth in vitro and in a murine model in vivo was analyzed.

Cell Cycle Analysis

Cells were infected at an MOI of 200–300 with the ADV-ΔE1 or ADV-p21 vectors or transfected with the p21 expression vector by DNA/liposome complexes. The cells were infected as above and harvested, washed with PBS twice, then fixed in 70% EtOH for 30 minutes of 4° C. The cells were treated with 1U Dnase-free RNase in 1 ml of PBS for 30 minutes at 37° C., and finally, resuspended in 0.05 mg/ml propidium iodide (made as a 10X stock in PBS, and cells were analyzed by flow cytometry using a FACScan model (Becton Dickinson). Fluorescence measurements were accumulated to form a distribution curve of DNA content. Fluorescence events due to debris were substracted before analysis.

Western Blot Detection of P21

$3-5\times10^6$ cells were harvested at the time points indicated, lysed with 1 ml of 50 mM Tris-Hcl (pH 6.8), 100 mM DTT, 2% SDS, 0.1% bromophenol blue, 10% glycerol, and boiled for 5 minutes. The samples were finally spun at 10,000 rpm for 5 minutes, and supernatants were collected. 20 $\mu$l were loaded into 15% SDS-PAGE and blotted into nitrocellulose membrane. p21 protein was visualized using an antipeptide rabbit polyclonal antibody (Santa Cruz) together with an antirabbit horseradish peroxidase secondary antibody and subsequent ECL chemiluminescent detection (Amersham).

Gene Transfer of P21

Cells were maintained in Dulbecco's modified eagle medium (DMEM) containing 10% fetal calf serum. The recombinant adenoviral vector, ADV-p21, was constructed by homologous recombination between sub360 genomic DNA, an Ad5 derivative with a deletion in the E3 region, and a p21 expression plasmid, pAd-p21. These recombinant adenoviral vectors have sequences in the E1A and E1B region deleted, impairing the ability of this virus to replicate and transform nonpermissive cells. Briefly, the pAd-p21 plasmid was prepared by introducing the Nru I and Dra III fragment from pRc/CMV-p21, kindly provided by Drs. D. Beach and G. Hannon (Xiong et al, Nature 366, 701 (1993); Serano et al, Nature 366, 704 (1993)) into the Bgl II site of pAd-Bgl II (Davidson et al, Nature Genet. 3, 219 (1994)) which had the left hand sequence of Ad5 genome, but not E1A and E1B. Virus was prepared as described previously (Ohno et al, Science 265, 781 (1994). The structure of these viruses was confirmed by Southern blotting. All recombinant viruses were propagated in 293 cells and purified as described (Davidson et al, Nature Genet. 3, 219 (1994)). Cesium chloride purified virus was dialysed against PBS, and diluted for storage in 13% glycerol-PBS solution to yield a final concentration of $1-3\times10^{12}$ viral particles/ml ($0.8-5\times10^{10}$ pfu/ml). All stocks were sterilized with a 0.45 $\mu$m filter and evaluated for the presence of replication competent adenovirus by infection at a MOI of 10 onto 3T3 cells. None of the stocks used in these experiments yielded replication-competent virus.

The eukaryotic expression plasmid, pRc/RSV p21, was prepared by introduction of the p21 cDNA from pRc/CMV-p21 into pRc/RSV (Invitrogen), and transfection of 293 cells performed by using calcium phosphate transfection (Perkins et al., manuscript submitted).

Bystander Assay

U373 human glioblastoma cells, kindly provided by Dr. K. Murazko, were infected with ADV-p21 (MOI 200). One day later, cells were trypsinized, counted, and mixed with the indicated number of uninfected U373 cells. 10,000 cells for each mixed population were plated into a 96 well disk. Five days later, the MTT assay (Mosman, J. Immunol. Methods 65, 55 (1983)) was performed to determine the proliferation rate of these cell populations.

Gene Transfer of p21 and Effect on Cell Cycle Progression in Malignant Cells.

Figure 1B:
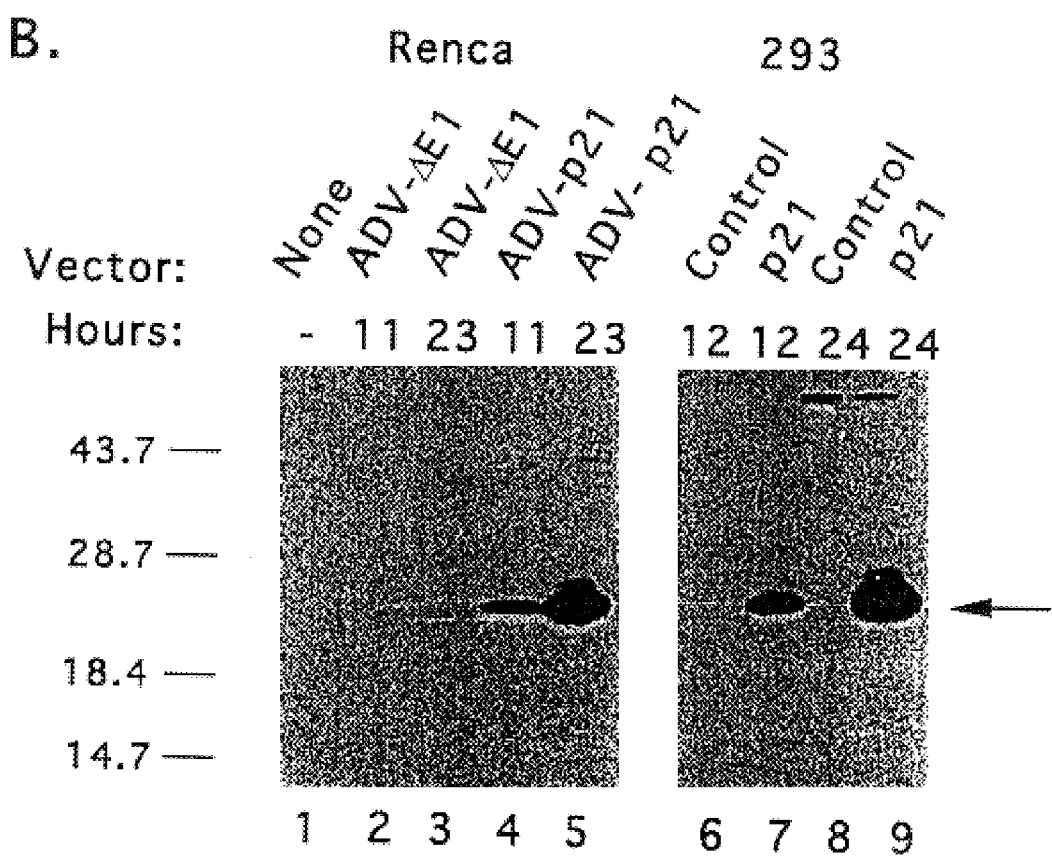

The effect of p21 on cell cycle distribution was determined in tumor cell lines by infection with an adenoviral vector, ADV-p21, or a similar E1 deletion virus with no recombinant p21, ADV-ΔE1. Expression of p21 in the adenoviral vector was regulated by the CMV enhancer/promoter and bovine growth hormone polyadenylation sequence. Expression of p21 within a representative malignant cell line, the B16BL6 melanoma, resulted in an accumulation of cells in the $G_0/G_1$ phase of the cell cycle, suggesting arrest predominantly at the G1/S boundary (FIG. 1a). Recombinant p21 expression was confirmed in murine (Renca) or human (293) renal cell carcinoma lines, and the murine (B16BL6) melanoma cell line by using Western blot analysis. Readily detectable protein expression from the adenoviral vector was achieved ~1 day after introduction of the gene (FIG. 1b, lanes 4,5,13,14 vs. 1–3,10–12). In addition, a eukaryotic expression plasmid regulated by the Rous sarcoma virus (RSV) enhancer/promoter and bovine growth hormone polyadenylation site showed comparable expression in 293 cells (FIG. 1b, lanes 7,9 vs. 6,8). In both cases, expression of the recombinant protein correlated with inhibition of cell division and other vectors with the same regulatory elements did not show the effects of p21 described here.

Differentiation and Morphologic Effects of p21.

Figure 2:
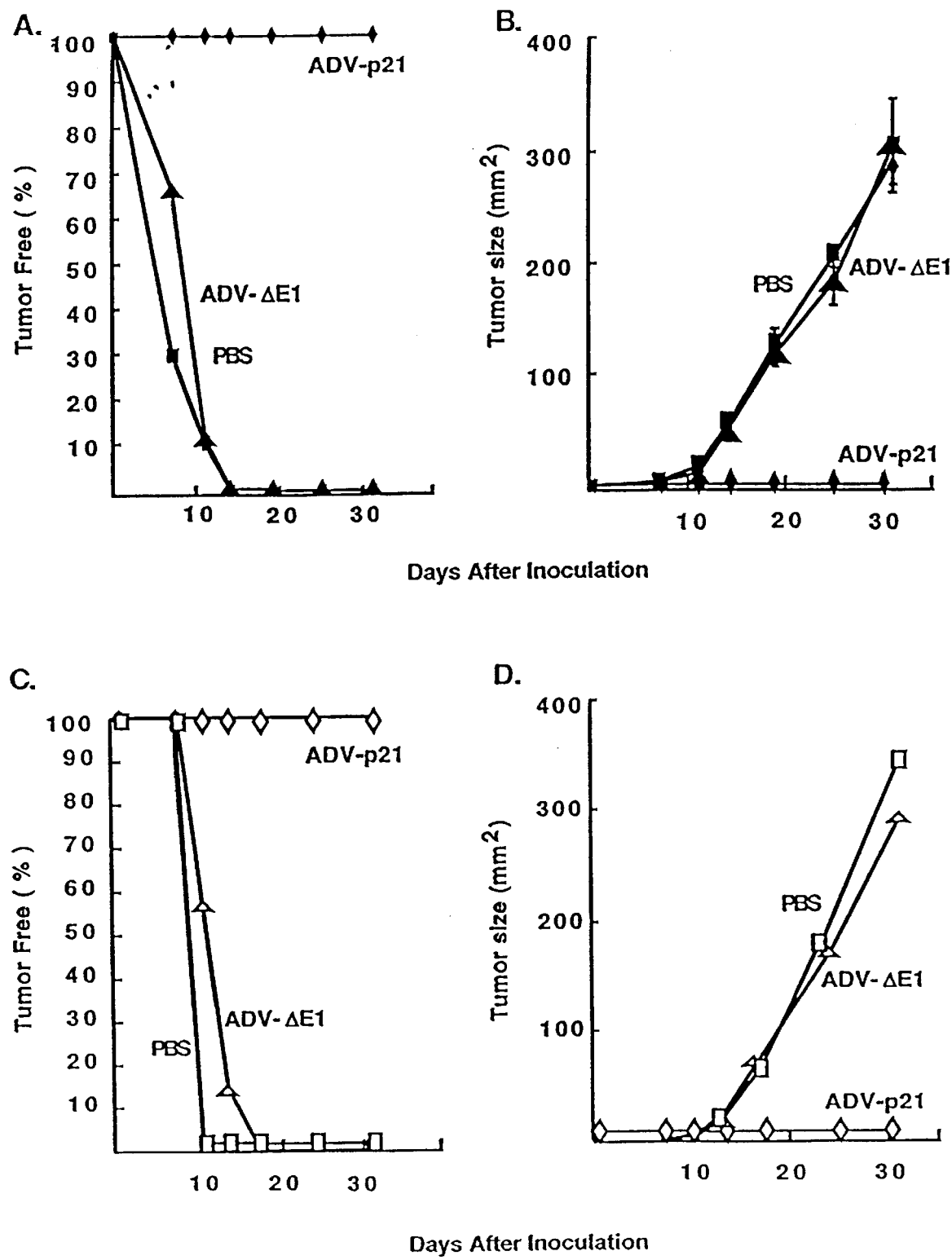
FIGS. 2A–2D are graphs depicting the inhibition of tumor growth following introduction of ADV p21 into Renca tumor cells followed by inoculation. The presence of tumor (A,C) and tumor diameter (B,D) were evaluated.
Figure 3:
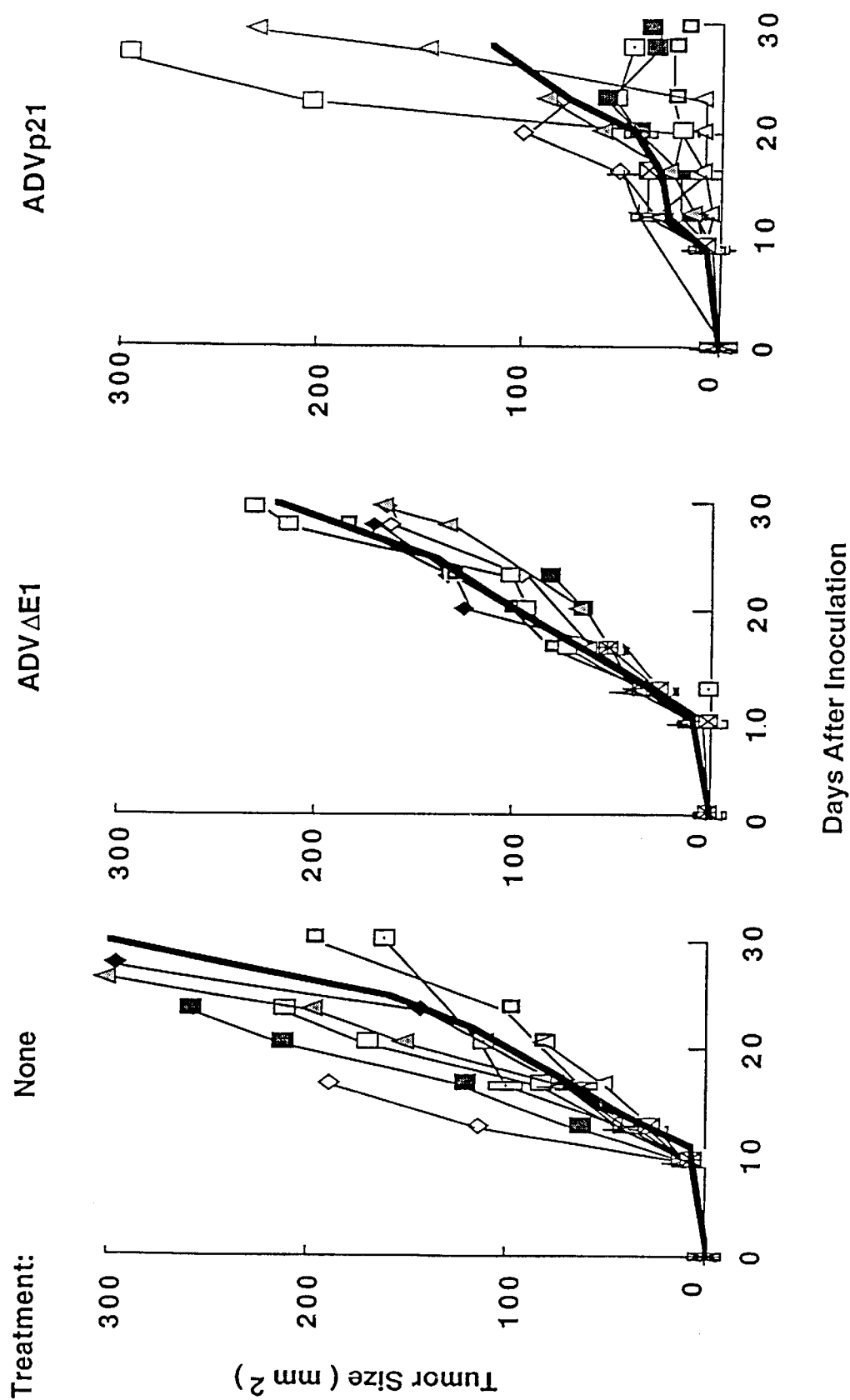
FIG. 3 are graphs depicting the effects of introduction of ADV p21 into established Renca tumor cells in vivo inhibits tumor growth. Tumor diameter was measured in two perpendicular dimensions using calipers.

When the effect of p21 on cell growth was examined in vitro, tumor cells infected with ADV-p21 showed morphological changes, such as an increased nuclear to cytoplasmic ratio, an increase in adherence and growth arrest, consistent with a differentiated phenotype (FIGS. 2,3). Human melanoma cells, UM-316, showed nuclear condensation and a >4-fold increase in melanosome formation by electron microscopy after infection with ADV-p21 (FIG. 2; $p\leq0.005$ by the Wilcoxon rank sum test). In these cells, an ~5-fold increase in melanin production was observed within 2 days after gene transfer in cells and supernatant fractions in vitro (FIG. 3).

Figure 4:
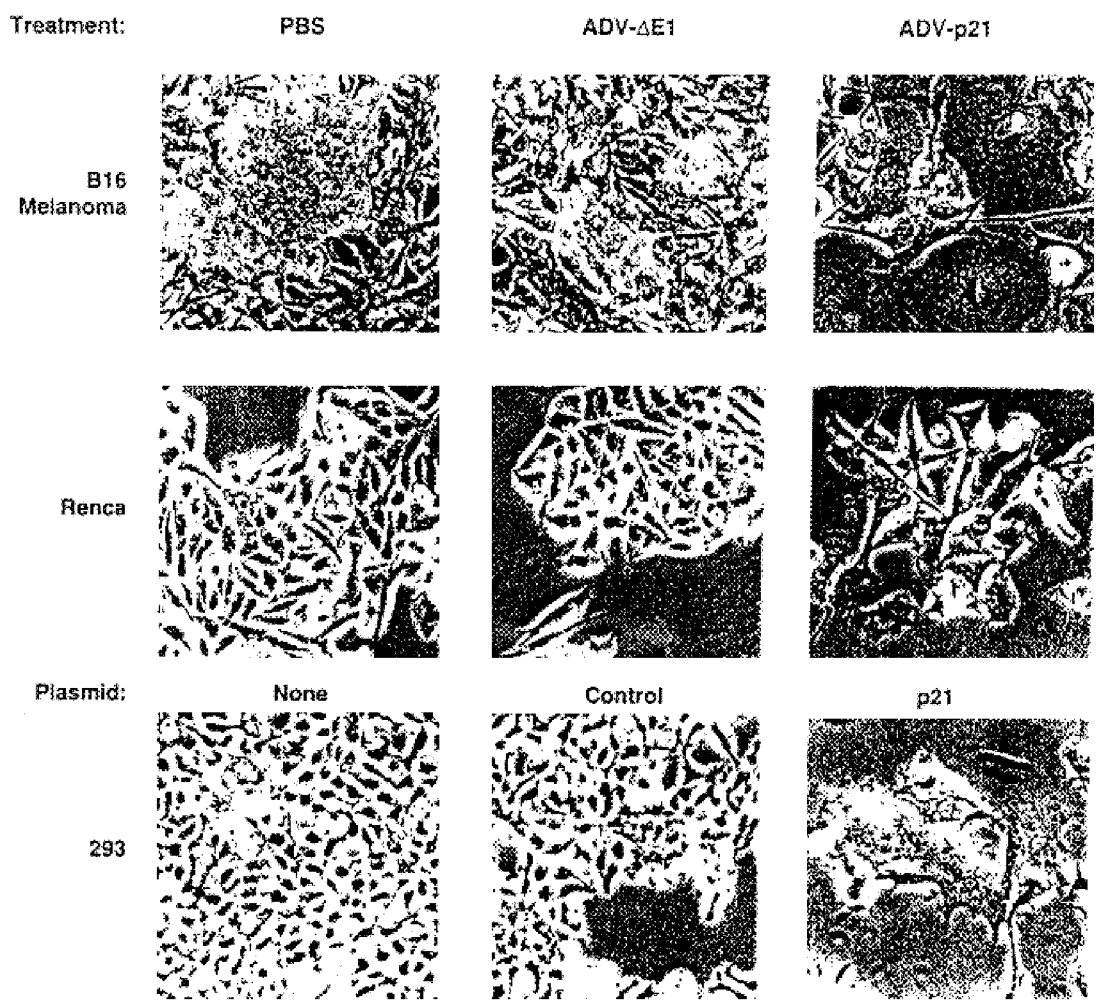
FIG. 4 are photographs depicting the in vitro effects of p21 on malignant cell growth and differentiation. Phase contrast microscopy was performed on the indicated cells 5 days after the indicated treatments. Magnification (20×).

In some lines, cell death was observed to follow terminal differentiation after extended cell culture, but there was no evidence of apoptosis, as determined by the pattern of DNA fragmentation (FIG. 4a), propidium iodine staining or TdT immunostaining. In addition, mixtures of uninfected and infected cells showed a lack of bystander effect (FIG. 4b), suggesting that gene transfer and expression in recipient cells was required and that efficient infection of p21 is required to eradicate growth of established tumors.

Inhibition of Tumor Cell Growth in Vivo.

Figure 5:
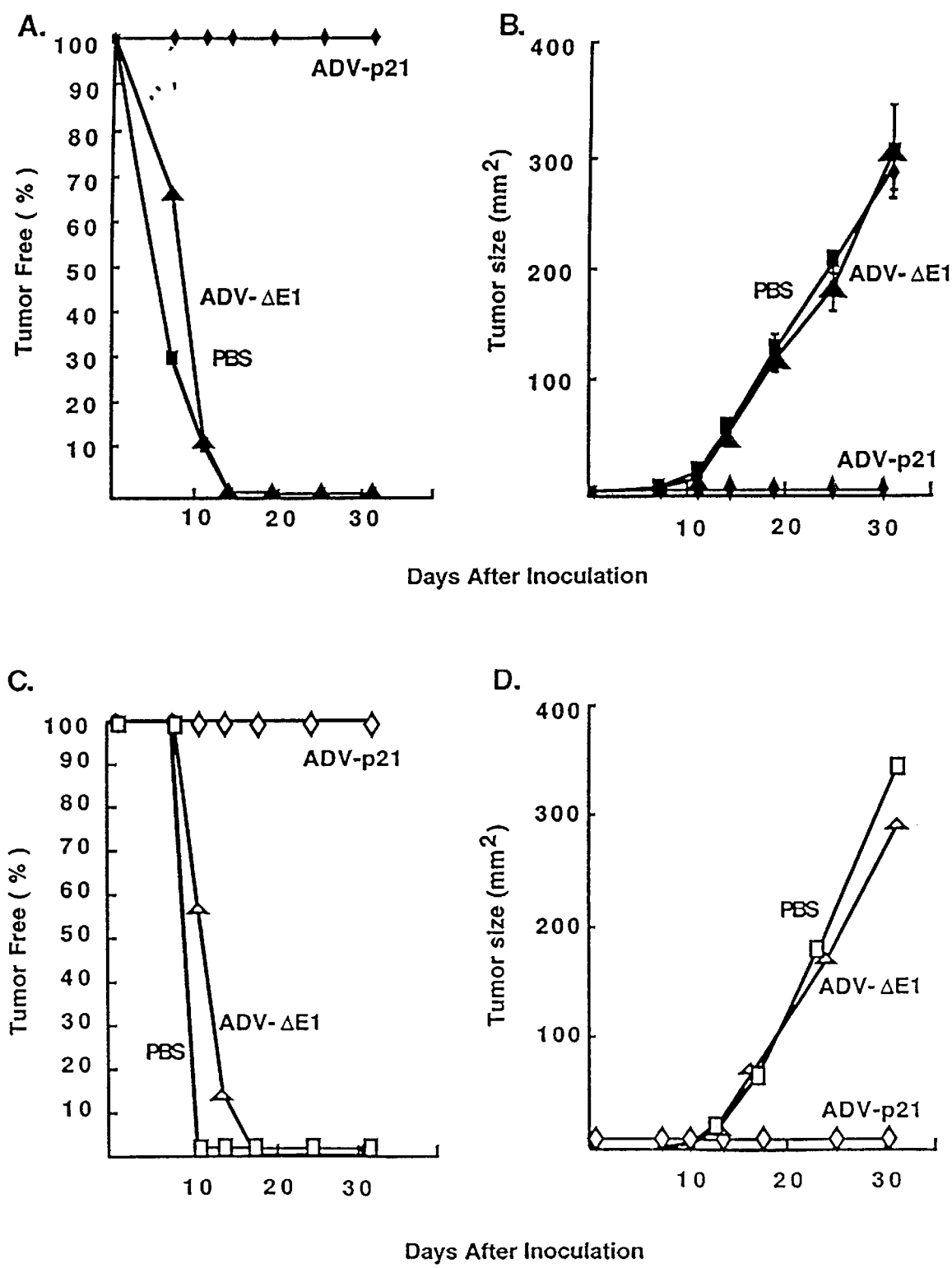
FIG. 5A–D are graphs depicting survival of mice with established tumors treated with ADV p21 or control vectors. BALB/c mice (a,b) or nu/nu CD-1 mice (c,d) were injected with Renca cells incubated in vitro with PBS (□,■), ADV-p21 (◊,♦) ADV-ΔE1 (Δ,▲) at an MOI of 300.

To assess the effect of p21 on the growth of malignant cells in vivo, Renca cells were infected with ADV-p21, an ADV-ΔE1 control, or incubated with phosphate buffered saline (PBS), and inoculated into recipient mice. p21 expression completely suppressed the growth of tumors in all animals inoculated with $2\times10^5$ cells (FIG. 5a,b). Because it remained possible that expression of p21 could alter the immunogenicity of infected cells and thus work through an immune mechanism, similar studies were undertaken in CD-1 nu/nu immunodeficient mice. Similar inhibition of tumor growth was observed in these animals (FIG. 5c,d), consistent with a direct effect on cell proliferation. To determine whether ADV-p21 could alter the growth of established tumors, Renca tumor nodules (~0.5 cm) were injected with either PBS, ADV-ΔE1, or ADV-p21. Direct transfer of adenoviral vectors encoding a human placental alkaline phosphatase reporter into established tumors caused infection of up to 95% of cells estimated by quantitative morphometry after 5 repeated daily injections of $10^{10}$ PFU. This treatment also inhibited tumor growth, and when injections were performed repetitively (5 daily injections, repeated after one week), could lead to long-term cure as determined by survival (>40 days) and the inability to detect macroscopic tumor in mice with previously detectable nodules. In both cases these results were statistically significant.

REFERENCES

1. Chang & Herskowitz, *Cell* 63, 999 (1990).
2. Jiang et al, *Oncogene* 9, 3397 (1994).
3. Steinman et al, *Oncogene* 9, 3389 (1994).
4. Zhang et al, *Mol. Biol. Cell* 4, 897 (1993).
5. Halevy et al, *Science* 267, 1018 (1995).
6. Peter & Herskowitz, *Cell* 79, 181 (1994).
7. Hunter & Pines, *Cell* 79, 573 (1994).
8. Noda et al, *Exp. Cell Res.* 211, 90 (1994).
9. Skapek et al, *Science* 267, 1022 (1995).
10. Parker et al, *Science* 267, 1024 (1995).
11. Xiong et al, *Nature* 366, 701 (1993).
12. Harper et al, *Cell* 75, 805 (1993).
13. Zhang et al, *Genes Dev.* 8, 1750 (1994).
14. Gu et al, *Nature* 366, 707 (1993).
15. el-Deiry et al, *Cell* 75, 817 (1993).
16. Li et al, *Oncogene* 9, 2261 (1994).
17. el-Deiry et al, *Cancer Res.* 54, 1169 (1994).
18. Di Leonardo et al, *Genes Dev.* 8, 2540 (1994).
19. Dulic et al, *Cell* 76, 1013 (1994).
20. Li et al, *Nature* 371, 534 (1994).
23. Symonds et al, *Cell* 78, 703 (1994).
25. Christman et al, *Cancer Res.* 43, 763 (1983).
26. Samid et al, *Cancer Res.* 52, 1988 (1992).
27. Pierce & Speers, *Cancer Res.* 48, 1996 (1988).
28. Leftwich & Hall, *Cancer Res.* 46, 3789 (1986).
29. Davidson et al, *Nature Gen.* 3, 219 (1993).
30. Ohno et al, *Science* 265, 781 (1994).

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A method of treating restenosis in a patient in need thereof comprising introducing in vivo into the patient's blood vessel at the site of restenosis a therapeutically effective amount of a composition comprising an expression vector comprising a gene which encodes p21 operatively linked to regulatory sequences directing the expression of the p21 gene, wherein the expression of the p21 gene results in the reduction of intimal hyperplasi in the blood vessel.

2. The method of claim 1, wherein the expression vector is a viral vector.

3. The method of claim 2, wherein the viral vector is an adenoviral vector.

4. The method of claim 1. wherein the patient is human.

5. The method of claim 1, wherein the expression vector is at a concentration of $10^{10}$ per ml.

6. A method of treating restenosis in a patient in need thereof comprising introducing into the patient's blood vessel at a site of restenosis a therapeutically effective amount of a composition comprising an expression vector comprising a fusion gene comprising a gene encoding p21 fused to a gene encoding a thymidine kinase, wherein the fusion gene is operatively linked to regulatory sequences directing the expression of the fusion gene, and wherein the expression of the fusion gene results in the reduction of intimal hyperplasia in the blood vessel.

7. The method of claim 6, wherein the expression vector is a viral vector.

8. The method of claim 7, wherein the viral vector is an adenoviral vector.

9. The method of claim 6, wherein the patient is human.

10. The method of claim 6, wherein the expression vector is at a concentration of $10^{10}$ per ml.

11. A method of treating restenosis in a patient in need thereof comprising introducing into the patient's blood vessel at the site of restenosis a therapeutically effective amount of a composition comprising an expression vector comprising a gene which encodes p21 operatively linked to regulatory sequences directing the expression of the p21 gene, and an expression vector comprising a second gene encoding thymidine kinase operatively linked to regulatory sequences directing the expression of the second gene;

wherein the expression vector comprising the gene encoding p21 and the expression vector comprising the second gene are the same or different and wherein the co-expression of the p21 gene and the thymidine kinase gene results in the reduction of intimal hyperplasia in the blood vessel.

12. The method of claim 11, wherein the expression vector is a viral vector.

13. The method of claim 12, wherein the viral vector is an adenoviral vector.

14. The method of claim 11, wherein the patient is human.

15. The method of claim 11, wherein the expression vector is at a concentration of $10^{10}$ per ml.

* * * * *

UNITED STATES PATENT AND TRADEMARK OFFICE
CERTIFICATE OF CORRECTION

PATENT NO. : 6,218,372 B1  Page 1 of 1
DATED : April 17, 2001
INVENTOR(S) : Gary J. Nabel et al.

It is certified that error appears in the above-identified patent and that said Letters Patent is hereby corrected as shown below:

<u>Column 12,</u>
Before line 11, delete "1." and substitute -- 1, -- in its place.

Signed and Sealed this

Twenty-eighth Day of May, 2002

Attest:

JAMES E. ROGAN
*Attesting Officer*  *Director of the United States Patent and Trademark Office*